(12) United States Patent
Hashimoto et al.

(10) Patent No.: US 9,217,130 B2
(45) Date of Patent: Dec. 22, 2015

(54) CELL CULTURE VESSEL AND METHOD OF PRODUCTION THEREOF

(75) Inventors: Takeshi Hashimoto, Nagoya (JP); Tsukasa Akasaka, Sapporo (JP); Atsuro Yokoyama, Sapporo (JP); Fumio Watari, Sapporo (JP)

(73) Assignee: MEIJO NANO CARBON CO., LTD., Nagoya-Shi (JP)

( * ) Notice: Subject to any disclaimer, the term of this patent is extended or adjusted under 35 U.S.C. 154(b) by 0 days.

(21) Appl. No.: 12/747,826

(22) PCT Filed: Dec. 11, 2008

(86) PCT No.: PCT/JP2008/072521
§ 371 (c)(1),
(2), (4) Date: Jun. 11, 2010

(87) PCT Pub. No.: WO2009/078333
PCT Pub. Date: Jun. 25, 2009

(65) Prior Publication Data
US 2010/0273263 A1 Oct. 28, 2010

(30) Foreign Application Priority Data
Dec. 14, 2007 (JP) ................................ 2007-323658

(51) Int. Cl.
*C12N 5/071* (2010.01)
*C12M 1/42* (2006.01)
*C12M 1/32* (2006.01)
*C12M 1/00* (2006.01)

(52) U.S. Cl.
CPC ............... *C12M 35/08* (2013.01); *C12M 23/12* (2013.01); *C12M 23/20* (2013.01)

(58) Field of Classification Search
USPC .......................... 435/402; 977/712, 892, 923
See application file for complete search history.

(56) References Cited

U.S. PATENT DOCUMENTS

| | | | |
|---|---|---|---|
| 6,346,023 | B1 | 2/2002 | Tsuboi et al. |
| 2006/0014275 | A1 | 1/2006 | Yanagisawa et al. |
| 2006/0052509 | A1 | 3/2006 | Saitoh |
| 2007/0067881 | A1 | 3/2007 | Lin et al. |
| 2007/0275627 | A1* | 11/2007 | Jung et al. ............. 445/51 |
| 2008/0297022 | A1* | 12/2008 | Maruyama et al. ......... 313/309 |
| 2009/0321688 | A1 | 12/2009 | Saitoh |
| 2010/0330358 | A1 | 12/2010 | Hashimoto |

FOREIGN PATENT DOCUMENTS

| | | |
|---|---|---|
| EP | 1 878 763 A2 | 1/2008 |
| JP | 2000-86219 A | 3/2000 |
| JP | 2004-75705 A | 3/2004 |
| JP | 2005-75661 A | 3/2005 |
| JP | 2005-89738 A | 4/2005 |
| JP | 2005-97499 A | 4/2005 |
| JP | 2005-130759 A | 5/2005 |
| JP | 2005-324999 A | 11/2005 |
| JP | 2006-16450 A | 1/2006 |
| JP | 2006-223273 A | 8/2006 |
| JP | 2007-39623 A | 2/2007 |
| JP | 2008-1898 A | 1/2008 |
| WO | WO 2006003027 A1 * | 1/2006 |

OTHER PUBLICATIONS

Aoki et al. (Carbon Nanotubes as Scaffolds for Cell Culture and Effect on Cellular Functions; Dental Materials Journal 26(2): 178-185; Mar. 2007).*
Gheith et al. (Single-Walled Carbon Nanotube Polyelectrolyte Multilayers and Freestanding Films as a Biocompatible Platform for Neuroprosthetic Implants; Advanced Materials; 17, 2663-2670; published online Oct. 11, 2005).*
McCullen et al. (Characterization of electrospun nanocomposite scaffolds and biocompatibility with adipose derived human mesenchymal stem cells; International Journal of Nanomedicine; Jun. 2007:2(2) 253-263).*
Park et al.; Carbon Nanotube Monolayer Patterns for Directed Growth of Mesenchymal Stem Cells; Advanced Materials; vol. 19; No. 18; pp. 2530-2534; published online Sep. 10, 2007.*
Advantec Japan Polycarbonate Membrane, captured online Mar. 18, 2006.*
Gibco Serum Free Brochure; published 2003.*
Hilding et al.; Dispersion of Carbon Nanotubes in Liquids; Journal of Dispersion Science and Technology; vol. 24, No. 1, pp. 1-41 (2003).*
International Preliminary Report on Patentability from parent International Application No. PCT/JP2008/072521.
Written Opinion from parent International Application No. PCT/JP2008/072521.
International Search Report for PCT/JP2008/072521.
Aoki, N. et al., Carbon nanotubes as scaffolds for cell culture and effect on cellular functions, Dental Materials Journal, Mar. 2007, vol. 26, No. 2, p. 178-185.
Bajaj, P. et al., Control of spatial cell attachment on carbon nanofiber patterns on polycarbonate urethane, International Journal of Nanomedicine, 2006, vol. 1, No. 3, p. 361-365.

\* cited by examiner

*Primary Examiner* — Antonio Galisteo Gonzalez
(74) *Attorney, Agent, or Firm* — J-Tek Law PLLC; Jeffrey D. Tekanic; Scott T. Wakeman

(57) ABSTRACT

Disclosed is a method of producing a cell culture vessel (10) having a carbon nanotube (CNT) layer (14) on its surface. The method comprises the steps of providing a vessel (12) having a predetermined shape; providing a CNT dispersion of a CNT material composed primarily of CNT dispersed in a dispersion medium at a concentration of not more than 50 mg/L; and forming the carbon nanotube layer (14) on the surface of the vessel (12). The formation of the CNT layer (14) is achieved by alternately repeating a supply step of applying the CNT dispersion solution to the vessel (12) and a drying step of drying the applied dispersion solution one or more times.

3 Claims, 4 Drawing Sheets

CELL CULTURE VESSEL AND METHOD OF PRODUCTION THEREOF

CROSS-REFERENCE

This application is the U.S. national stage of International Application No. PCT/JP2008/072521 filed Dec. 11, 2008.

TECHNICAL FIELD

The present invention relates to technology employing carbon nanotubes in the field of cell cultivation.

This application claims priority from Japanese Patent Application No. 2007-323658, filed on Dec. 14, 2007, the entire contents of which are hereby incorporated by reference.

BACKGROUND ART

Cell culture vessels which have been surface treated to enhance properties such as the ability of cells to attach and spread thereon are known. For example, polystyrene dishes which have been subjected to surface treatment (typically, surface hydrophilicity-enhancing treatment), such as carboxyl group treatment, collagen treatment or polylysine treatment are commercially sold.

Conventional technology documents relating to the use of carbon nanotubes (referred to below as "CNT") in the field of cell cultivation include Patent Documents 1 to 3 below.

Patent Document 1: Japanese Patent Application Laid-open No. 2005-130759

Patent Document 2: Japanese Patent Application Laid-open No. 2006-223273

Patent Document 3: Japanese Patent Application Laid-open No. 2007-39623

DISCLOSURE OF THE INVENTION

However, such conventional technology either cannot be applied to the surface treatment of existing vessels (e.g., polystyrene dishes), or when applied in a simple manner is unlikely to elicit sufficient treatment effects (e.g., cell growth-promoting effects).

In one aspect of the present teachings, a method of producing a vessel which has been subjected to surface treatment using CNT and is suitable for use in cell cultivation (a cell culture vessel). In another aspect of the present teachings, a cell culture vessel is provided that has been subjected to such surface treatment. In further aspect of the present teachings, a CNT thin-film is prepared which can be used for surface treating (surface modifying) such vessels and other substrates and is suitable for culturing cells (the CNT thin-film typically possessing a cell growth-promoting activity), and a method of producing such a thin-film is also provided.

A representative method of producing a cell culture vessel having a CNT layer on a surface thereof may include providing a vessel having a predetermined shape; providing a CNT dispersion of a CNT material composed primarily of CNT dispersed at a concentration of not more than about 50 mg/L (preferably not more than about 20 mg/L) in a dispersion medium; and forming a CNT layer on the surface of the vessel. Here, the formation of the CNT layer is carried out by alternately repeating once or twice or more times a supply step of applying the dispersion to the vessel and a drying step of drying the applied dispersion.

By using such a low-concentration CNT dispersion, a CNT layer which has a good surface state (e.g., wherein the CNT is well oriented in the planar direction; that is, which is highly planar) can be formed. Such a surface state is suitable for cell cultivation (typically, growth). Accordingly, a good cell growth-promoting activity can be achieved with a CNT layer formed by this method (and, in turn, with a cell growth vessel having such a CNT layer formed on a surface thereof).

The supply step is preferably carried out in such a way that the CNT material included in the dispersion applied in each performance of the supply step is not more than about 0.1 μg per $cm^2$ of surface area of the CNT layer formed (and preferably not more than about 0.05 μg/$cm^2$ per supply in the step). By applying the CNT material in only a small amount at a time as a low-concentration CNT dispersion, a CNT thin-film having a better surface state can be formed. By repeating the above supply step and drying step and thereby building up such thin-films, a CNT layer of the desired thickness can be formed. In this way, regardless of the total thickness of the CNT layer to be formed, a CNT layer having a better surface state (i.e., more suitable for cell cultivation) can be formed.

In a preferred embodiment of the method disclosed herein, the supply step and the drying step are repeated at least about 20 times. That is, the CNT layer is formed by building up at least about 20 CNT thin-films, each of which is formed in one performance of the supply step followed by a drying step. The effects arising from the use of the invention can be especially well manifested through this embodiment.

It is preferable for the formation of the CNT layer to be carried out under low-humidity conditions at a relative humidity of not more than about 30%. In this way, a CNT layer better suited for cell cultivation can be formed.

The CNT dispersion typically exhibits a light gray appearance overall. When the CNT material included in this dispersion is in a highly dispersed state, the color of the dispersion on visual examination is uniform (e.g., granular or fleck-like agglomerates are not observed). In a preferred embodiment of the method disclosed herein, in the supply step, the dispersion is applied to the vessel in a highly dispersed state (in other words, in a highly dispersed state at a level where no agglomerates are visible). In this way, a CNT layer better suited to cell cultivation can be formed.

It is preferable for the CNT included in the dispersion to be primarily monolayer CNT. By using such a dispersion, a CNT layer better suited to cell cultivation can be formed.

A cell culture vessel may be manufactured by any of the methods disclosed herein. Such a cell culture vessel may be advantageously used in applications where a culture medium (typically a culture broth) is placed within the vessel (typically on a CNT layer), and various types of cells (which may be tissue fragments) are cultured therein. Such a vessel is especially preferred for applications involving cell cultivation in a low-serum culture medium (understood here in a sense which is inclusive of serum-free media). The present teachings thus provide, in another aspect, a cell culturing method which is characterized by culturing cells using any of the cell culture vessels disclosed herein (which may be cell culture vessels produced by any of the methods disclosed herein).

A method of producing a CNT layer (typically a thin-film type layer) possessing cell growth-promoting activity is also disclosed. In this production method, the CNT layer is formed by alternately repeating once or twice or more times a supply step of applying to a substrate a CNT dispersion of a CNT material composed primarily of CNT dispersed at a concentration of not more than about 50 mg/L (more preferably not more than about 20 mg/L) in a dispersion medium and a drying step of drying the applied dispersion. By using a low-concentration CNT dispersion in this way, a CNT layer having a good surface state and cell growth activity can be obtained. The supply step is preferably carried out in such a way that the CNT material included in the dispersion applied in each performance of the supply step is not more than about 0.1 μg per cm² of the surface area of the CNT layer formed (and more preferably not more than about 0.05 μg/cm² per supply in the step). In this way, regardless of the total thickness of the CNT layer to be formed, a CNT layer having a better surface state (capable of achieving a higher cell growth-promoting activity) can be formed.

A CNT layer possessing cell growth-promoting activity may be produced by any of the methods disclosed herein. Such a CNT layer may be advantageously used in applications where a culture medium (typically a culture broth) is placed on the layer and various types of cells (which may be tissue fragments) are cultured therein. Such a CNT layer is especially preferred for applications involving cell cultivation in a low-serum culture medium. The present teachings thus provide, in another aspect, a cell culturing method which is characterized by culturing cells on any of the CNT layers disclosed herein (which may be CNT layers produced by any of the methods disclosed herein). The present teachings thus provide, according to yet another aspect, a method of producing a cell culture (inclusive of cell clusters and organized cultures, and not limited to a specific shape) by employing any of the cell culturing methods disclosed herein.

BEST MODE FOR CARRYING OUT THE INVENTION

Figure 1:
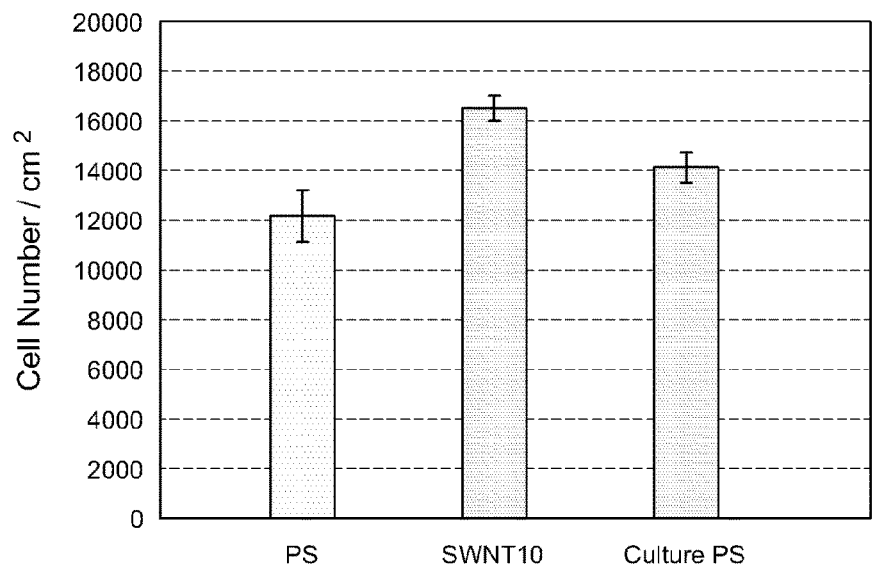
FIG. 1 is a graph showing the results of culture assays according to Example 1.

Preferred embodiments of the invention are described below. Matters which are not specifically mentioned in the Specification but which are necessary for practicing the invention will be understood as matters of design by persons of ordinary skill in the art based on prior art in the field. The present invention can be practiced based on the details disclosed in the Specification and common general technical knowledge in the field.

In the technology disclosed herein, the CNT dispersion used to form the CNT layer may be one prepared using a CNT material obtained by any of various methods. That is, the CNT material used to prepare the CNT dispersion may be one that has been suitably selected from among CNT materials containing CNT manufactured by any of various methods, such as arc discharge processes, laser vapor deposition processes and chemical vapor deposition processes (CVD). The CNT included in the CNT material may be monolayer CNT, multilayer CNT, or a mixture containing these in any proportions.

In addition to CNT, the CNT material also may include carbon ingredients such as amorphous carbon that does not form tubes (impure carbon), and metal catalyst, etc. Carbonaceous products obtained by various methods such as those mentioned above (e.g., an arc discharge process) may be used directly as the CNT material, or may be used as the CNT material after being subjected to any type of post-treatment (e.g., purification treatment such as amorphous carbon removal or metal catalyst removal). The length of the CNT making up the CNT material is typically at least about 1 μm, and preferably at least about 5 μm (typically from about 5 μm to several tens of micrometers). This length may even be about 10 μm or more (typically from about 10 μm to several tens of micrometers).

Various media which are in a liquid state in a temperature range of about room temperature (e.g., 23° C.) may be used as the dispersion medium for dispersing this CNT material. A dispersion medium composed primarily of water, an organic solvent or a mixed solvent thereof is preferred. One or more types of organic solvent selected from among common organic solvents which are in a liquid state in a normal temperature range may be used as the organic solvent. The type and composition of the solvent making up the above liquid medium may be selected as appropriate for the objects and embodiments of the invention. Water or a mixed solvent composed primarily of water is one typical example that may be suitably selected as the solvent making up the above dispersion medium. Other preferred examples include lower alcohols having from 1 to about 4 carbons (e.g., ethanol). In addition to a solvent, the above dispersion media may also include, when necessary, various additives as secondary ingredients. Examples of such additives include surfactants, antioxidants, viscosity modifiers, pH adjustors and preservatives.

As the CNT dispersion used in the technology disclosed herein, preferred use may be made of a dispersion in which the CNT material accounts for at least about 90 wt % (and more preferably at least about 95 wt %, such as about 98 wt % or more) of the nonvolatile content (CNT layer-forming ingredients) of the dispersion. For example, this may be a composition containing substantially no polymer ingredients (generally organic binders, etc. used for the purpose of binding the dispersed substance (in this case, the CNT material)). By using a CNT dispersion of such a composition, a CNT layer containing the CNT material in a high proportion can be formed. Especially good cell growth-promoting effects can be achieved by means of such a CNT layer.

In the technology disclosed herein, use is made of a CNT dispersion of the above CNT material dispersed within the above dispersing medium at a low concentration (e.g., at a concentration of not more than about 100 mg/L). Typically, a CNT dispersion containing the above CNT material at a concentration of not more than about 50 mg/L in the dispersing medium is used. It is preferable to use a CNT dispersion having a CNT material concentration of not more than about 20 mg/L (and more preferably not more than about 15 mg/L, such as about 10 mg/L). By using a CNT dispersion having such a low concentration, a CNT layer which is more suitable for cell cultivation (e.g., which better promotes cell growth) can be formed. If the concentration of the CNT material used is too high, a cell growth-promoting effect will not be exhibited in the resulting CNT layer, or the degree of this effect will tend to be small. Although there is no particular lower limit in the preferred CNT material concentration in the CNT dispersion, because the number of repetitions of the supply steps and drying steps (also referred to below as the "supply and drying steps") required to form a CNT layer of the desired thickness increases as the concentration becomes lower, from the standpoint of productivity and the like, it is generally suitable to use a CNT dispersion having a CNT material concentration of at least about 0.1 mg/L (e.g., about 1 mg/L or more).

Techniques for dispersing the CNT material in the dispersion medium include any one, or suitable combinations of two or more of, for example, a stirring treatment in which a mixture, wherein the CNT material and the dispersant coexist, is mechanically stirred (e.g., stirring treatment carried out using an agitator of a type that rotates an agitator element of a suitable shape, such as a propeller, within the mixture), an ultrasonic treatment, in which ultrasonic vibrations are applied to the mixture, and a shaking treatment, in which the mixture is shaken. The ultrasound used for such ultrasonic treatment preferably has, for example, a frequency of from about 20 kHz to about 40 kHz. It is preferable to carry out treatment using a sonicator capable of generating ultrasonic vibrations of a given frequency under output conditions of from about 80 W to about 200 W. When the output is too low, the treatment efficiency has a tendency to decrease, and when the output is too high, CNT damage tends to result. The type of sonicator used (e.g., mode of ultrasound generation, device configuration) is not subject to any particular limitation; a suitable device may be selected according to the objects and embodiments of the invention.

Figure 7:
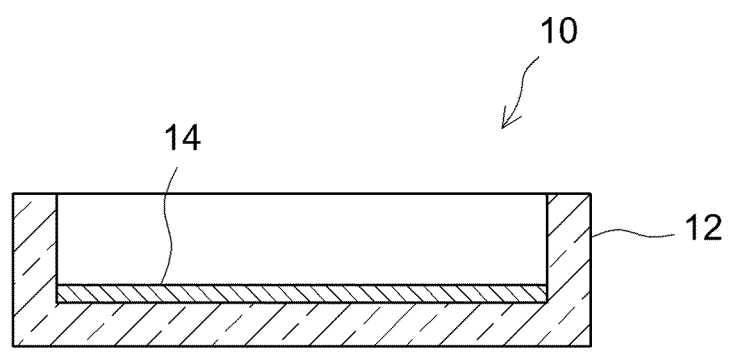
FIG. 7 is a schematic cross-sectional diagram showing the construction of a cell culture vessel according to the present invention.

Various known substrates used for culturing cells may be employed without particular limitation as the substrate (support) on which the CNT layer is formed in the technology disclosed herein. The material making up the substrate may be, for example, a polymeric material, glass (typically, silica glass), silicon, ceramic or a metal material. Preferred examples of polymeric materials include polystyrenes, polyolefin resins such as polyethylenes and polypropylenes, polyacetals, polyamides, polycarbonates, ABS resins, polyimides, fluorinated resins, and derivatives thereof. In addition to substrates made of such synthetic resins, use may also be made of substrates made of, for example, silk fibroin film. Preferred examples of ceramics include silica, alumina, and apatite. Preferred examples of metal materials include gold, silver, copper, and alloys thereof. No particular limitation is imposed on the shape of the substrate; substrates of various shapes adapted to the object (embodiment) of cultivation and the cell culture application may be suitably selected and used. For example, advantageous use may be made of a substrate having a smooth-surfaced plate-like or cylindrical portion. Preferred examples of such substrates include various already-known vessels such as dishes, flasks, tubes and well plates that are generally used for cell cultivation. By means of the technology disclosed herein, there is provided, as shown in FIG. 7 for example, a cell culture vessel 10 composed of a vessel 12 of a predetermined shape having a CNT layer 14 on a surface thereof. This cell culture vessel 10 may be of a form, for example, in which a CNT layer 14 has been provided over the entire bottom surface on the inside of a dish-like (typically, a shallow cylindrical) vessel 12.

In the technology disclosed herein, a CNT layer is formed on the surface of the substrate (typically, at least part of the inside surface of the vessel, such as the entire bottom surface on the inside of the vessel) by repeating as necessary the supply step of applying the above CNT dispersion to this substrate (vessel) and the drying step of drying the applied CNT dispersion. The thickness of the CNT layer ultimately formed is not subject to any particular limitation. Generally, it is preferable to form a CNT layer containing at least about 0.01 µg of CNT material per $cm^2$. With a CNT layer having a CNT material weight of at least about 0.02 $\mu g/cm^2$, a more preferable result (typically, a higher cell growth-promoting activity) can be achieved. Although there is no particular upper limit on the weight of the CNT material included per $cm^2$ of the CNT layer, from the standpoint of material costs and productivity, it is generally suitable to set the weight to not more than about 50 $\mu g/cm^2$ (e.g., not more than about 10 $\mu g/cm^2$).

It is suitable to carry out the above supply steps in such a way as to apply a small amount (e.g., not more than about 0.5 $\mu g/cm^2$, and typically not more than about 0.2 $\mu g/cm^2$) of CNT material in each performance of the supply step, and preferable to carry out the supply steps in such a way that the amount of CNT material applied in each performance of such supply step is not more than about 0.1 $\mu g/cm^2$ (more preferably not more than about 0.05 $\mu g/cm^2$ per supply step; e.g., not more than about 0.03 $\mu g/cm^2$ per supply step). Although there is no particular lower limit in the preferred CNT material weight, because a smaller material weight results in an increase in the number of repetitions of the supply and drying steps required to form a CNT layer of the desired thickness, from the standpoint of production efficiency and the like, it is generally appropriate to set the CMT material weight supplied in each performance of the supply step to at least about 0.001 $\mu g/cm^2$ (e.g., at least about 0.005 $\mu g/cm^2$). By way of illustration, when an ordinary dish having a diameter of 60 mm is used and a CNT layer is formed over the entire bottom surface of the dish, the weight of the CNT material applied to the dish in each performance of the supply step may be set to, for example, about 10 µg or less, preferably about 3 µg or less, and more preferably about 2 µg or less (e.g., about 1 µg or less). The lower limit on the CNT material applied to the above dish in each performance of the supply step is preferably, for example, at least about 0.02 µg, and more preferably at least about 0.1 µg.

In a preferred embodiment of the technology disclosed herein, the CNT layer may be formed by repeating the above supply and drying steps two or more times. The number of such repetitions is more preferably ten or more times (e.g., 20 or more times). According to this embodiment, a CNT layer composed of built-up CNT thin-films formed by each supply and drying step is obtained. The CNT layer having this built-up structure, when compared with a CNT layer formed by, for example, applying once (in one performance of the supply step) the same amount of CNT material as in the built-up CNT layer and drying, is able to achieve a better surface state (and thus a higher cell growth activity). The number of repetitions is not subject to any particular upper limit, although from the standpoint of production efficiency and the like, it is generally appropriate for the number of repetitions to be not more than about 1,000 times (e.g., not more than about 500 times).

The amount of CNT material applied in each supply step may be set in such a way that, based on, for example, the weight of the CNT material to be included in 1 $cm^2$ of the CNT layer to be produced, this quantity of CNT material is applied in divided amounts in a suitable number of supply steps. The quantity of CNT material supplied in each supply step may be the same or may be different. For example, after forming a CNT thin-film (first layer) in a single supply and drying step using a CNT dispersion containing about 50 to 70 wt % of the CNT material to be used to form the CNT layer, the formation of the CNT layer may be completed by repeating at least once (typically two or more times, and preferably ten or more times) a supply and drying step in which the weight of CNT material applied in each performance of the supply step has been set in the preferred range indicated above.

Suitable use may be made of various already-known coating methods, such as methods involving the dropwise addition of the CNT dispersion to the substrate and spray coating methods, as the method of applying the CNT dispersion to the substrate (vessel) in the supply step. To spread the applied CNT dispersion uniformly over the region where the formation of the CNT layer is intended, the substrate may, if necessary, be tilted or rotated. For example, advantageous use may be made of common spin coating.

The drying step may be carried out by natural drying (air drying), although, where necessary, suitable use may be made of means to promote drying such as heating, forced air or reduced pressure. Generally, preferred use may be made of an embodiment in which the applied CNT dispersion is naturally dried.

The formation of the CNT layer in the supply and drying step may be advantageously carried out at normal temperature and pressure. By forming the CNT layer in an environment having a relative humidity of not more than about 40% (preferably not more than about 30%, and more preferably not more than about 20%), even better results (e.g., a higher cell growth-promoting activity) can be achieved. No particular lower limit is imposed on the preferred relative humidity at the time of CNT layer formation, although a relative humidity of about 5% or more is generally appropriate from the standpoint of, for example, production costs and the ease of maintaining the humidity.

The CNT layer or cell growth vessel having such a CNT layer disclosed herein (which may be a CNT layer or a cell growth vessel produced by any of the methods disclosed herein) may be advantageously used in applications for growing various types of cells. For example, they may be used for culturing any of the following: adherent cells such as epithelial cells, fibroblasts, vascular endothelial cells, hepatocytes, nerve cells and cancer cells; and suspended cells, including stem cells such as embryonic stem cells (ES cells) and myeloid stem cells.

Various types of known culture media may be employed without particular limitation as the medium (typically a culture broth) used for cultivation. For example, use may be made of Eagle's media, RPMI media, HaM's media, Fisher's media and MCDB media of various compositions. Examples of Eagle's media include BM media, MEM media and DMEM media. Of these, in the cultivation of mammalian cells, preferred use may be made of, for example, Eagle's media.

The culture medium may be a medium containing about 5 to 10% serum, or may be a low-serum medium (inclusive of serum-free media containing substantially no serum) having a serum concentration of less than 5%. The CNT layer or the cell culture vessel having such a CNT layer disclosed herein may be also advantageously used in cultivation using such a low-serum medium, enabling excellent cell growth-promoting effects to be achieved. These are particularly appropriate in applications which carry out cultivation at a serum concentration of 3% or less (typically from 0 to 3%), such as under 1% serum concentration conditions or 2% serum concentration conditions.

The technique for culturing cells using such a culture medium is not subject to any particular limitation. Culturing methods, culturing conditions and the like (e.g., the composition and concentration of the medium, the incubation temperature and incubation period) may be suitably selected in accordance with the cells to be cultured or the target cell culture. For example, in the case of ordinary mammalian cells, preferred use may be made of an incubation temperature of from room temperature to a temperature which is about the body temperature of the mammal (i.e., about 20 to 40° C., and preferably about 33 to 38° C.) and an incubation period of from about a half-day to about one month (e.g., from one to two weeks). To prevent a rise in the pH of the medium, it is preferable to carry out the cultivation while keeping the $CO_2$ concentration within the culture atmosphere substantially fixed (e.g., from 3 to 10%, and especially about 5%).

Representative examples of the present teachings are described below, although these examples are not intended to limit the scope of the invention.

Example 1

Production of Cell Culture Vessel

A pair of stick-like electrodes (anode and cathode) composed of graphite containing uncombined iron (1 mol %) were prepared, and arranged opposite to each other, with an interval therebetween of from about 0.5 mm to about 5 mm, within a reaction vessel. The interior of the reaction vessel was adjusted to an atmosphere having a hydrogen gas ($H_2$) partial pressure of about $1.3 \times 10^4$ Pa and an argon gas (Ar) partial pressure of about $1.3 \times 10^4$ Pa. Next, a voltage of about 20 to 40 V was applied using a direct-current power supply connected between the pair of electrodes and a current of about 30 to 70 A was supplied from the power supply to generate an arc discharge between the two electrodes. By means of this arc discharge, carbon was made to evaporate from the anode, thereby obtaining a cobweb-like product containing monolayer CNT. The proportion of monolayer CNT included in the product was at least 70 mol %.

Next, 0.5 mg of this product (CNT material, also referred to below as "SWNT material") was added to 100 mL of anhydrous (99.5%) ethanol, and ultrasonic dispersion treatment, which entailed applying 35 kHz ultrasonic vibrations for 30 minutes, was carried out. In this way, a CNT dispersion containing a 5 mg/L concentration of the above SWNT material (also referred to below as the "SWNT dispersion") was prepared. This SWNT dispersion exhibited a uniformly light gray appearance with no visible agglomerates.

Immediately after the ultrasonic dispersion treatment, 50 µL (containing therein 0.25 µg of SWNT material) was collected from the SWNT dispersion, then was added dropwise onto a 60 mm diameter polystyrene Petri dish (a dish with an untreated surface, manufactured by Corning; abbreviated below as "PS dish") and was made to spread over the entire bottom surface of the dish, following which the SWNT dispersion thus added was dried (in this case, air-dried). By means of this first supply and drying step, a CNT thin-film was formed on the bottom surface of the PS dish.

Next, another 50 µL was collected from the SWNT dispersion prepared above (which continued to be in a highly dispersed state with no visible agglomerates), then added dropwise onto the CNT thin-film (first layer) formed in the above first supply and drying step and dried (second supply and drying step), thereby forming a CNT thin-film (second layer) on the first layer. By repeating this procedure a total of 40 times (the total amount of SWNT material supplied to the 60 mm diameter dish (i.e., the weight of the coating of CNT material)=10 µg), a cell culture vessel composed of a PS dish having a CNT layer formed on the bottom surface thereof (in other words, coated with CNT material) was produced. This vessel is referred to below as "SWNT10 dish".

Figure 6:
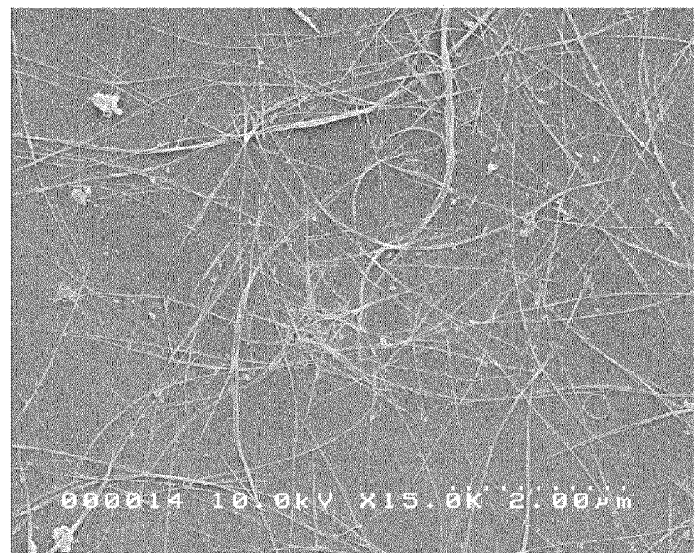
FIG. 6 is a scanning electron micrograph of a SWNT10 dish surface.

FIG. 6 shows an image obtained by examining the surface of this SWNT10 dish with a scanning electron microscope (SEM). As shown in FIG. 6, a monolayer CNT was confirmed to be attached to the surface of the PS dish in a well-dispersed state (bundles in a thoroughly unattached state).

Culture Assays

The SWNT10 dish produced above was subjected to UV sterilization treatment by a conventional method, after which the following culture assay was carried out using this dish. That is, 4 mL of a culture broth prepared by adding 10 wt % of fetal bovine serum (FBS) and 1 wt % of PSN (an antibiotic mixture) to Dulbecco's modified Eagle's medium (DMEM) was placed in a SWNT10 dish. This was inoculated with $1 \times 10^4$ cells/dish of SaOs-2 (osteoblast-like cells from a human sarcoma), and cultured for one week at 37° C. and 5% $CO_2$.

SaOs-2 was similarly cultured using, instead of a SWNT10 dish, the above-described PS dish (i.e., a PS dish on which a surface treatment to form a CNT layer was not carried out (untreated PS dish)) and a PS dish for cell culture manufactured by Corning (referred to below as "Culture PS dish"). The above Culture PS dish was subjected to a surface treatment (hydrophilizing treatment such as corona discharge treatment) for cell cultivation.

Following the end of the incubation period, the number of cells was counted by examining the culture broth under an optical microscope. The number of cells per $cm^2$ of the culture surface area was calculated from these results.

The results of the above culture assays are shown in Table 1 and FIG. 1. Here, the vertical axis in FIG. 1 represents the number of cells per $cm^2$.

TABLE 1

| Dish | Cell number ($\times 10^3/cm^2$) |
|---|---|
| SWNT10 | 16.7 |
| PS | 12.2 |
| Culture PS | 14.2 |

As shown in Table 1 and FIG. 1, with cultivation using a SWNT10 dish, increases in cell count superior to both the PS dish and the Culture PS dish were observed. Specifically, with a SWNT10 dish, a cell growth-promoting effect of about 1.4 times that of the PS dish and about 1.2 times that of the Culture PS dish were achieved.

Using a Culture PS dish instead of a PS dish in the production of the SWNT10 dish (i.e., repeating the supply and drying steps 40 times, in which 50 µL of the above SWNT dispersion was supplied to and dried each time on a Culture PS dish), a cell culture vessel (referred to below as a "SWNT10/CPS dish") was produced in which a total of 10 µg of SWNT material had been coated on the Culture PS dish. With this SWNT10/CPS dish, a SaOs-2 culture assay was carried out in the same manner as above. As a result, compared with an untreated Culture PS dish, cell growth was found to be even further promoted in the SWNT10/CPS dish (that is, even in a Culture PS dish, a cell growth-promoting effect was demonstrated due to the formation of a CNT layer).

In addition, 1 mg of the above SWNT material was added to 100 mL of anhydrous (99.5%) ethanol, and an ultrasonic dispersion treatment was carried out in the same way as above to prepare a SWNT dispersion having a concentration of 10 mg/L (in which agglomerates were not observed). Next, the step in which 50 µL of this SWNT dispersion was supplied to and dried on the above PS dish was repeated 20 times (total weight of SWNT material=10 µg) to similarly produce a cell culture vessel. Using this cell culture vessel, SaOs-2 culture assays were carried out in the same way as above. From the results, it was confirmed that, as with the SWNT10 dish produced using a SWNT dispersion having a concentration of 5 mg/L, cell growth-promoting effects are obtained.

Example 2

Except for changing to four times the number of times the step in which 50 µL of the above SWNT dispersion is supplied and dried (total weight of SWNT material=1 µg), a cell culture vessel having a CNT layer formed on the bottom surface of a PS dish was produced by the same procedure as for the SWNT10 dish produced in Example 1. This vessel is referred to below as the "SWNT1 dish". In addition, except for setting the number of times the above supply and drying step was repeated to 200 times (total weight of SWNT material=50 µg), a cell culture vessel (SWNT50 dish) was produced in the same way as described above.

Also, a cell culture vessel (SWNT100 dish) was produced by setting the amount of SWNT dispersion supplied in each performance of the supply step to 100 µL, and repeating the supply and drying step 200 times (total weight of SWNT material=100 µg).

Figure 2:
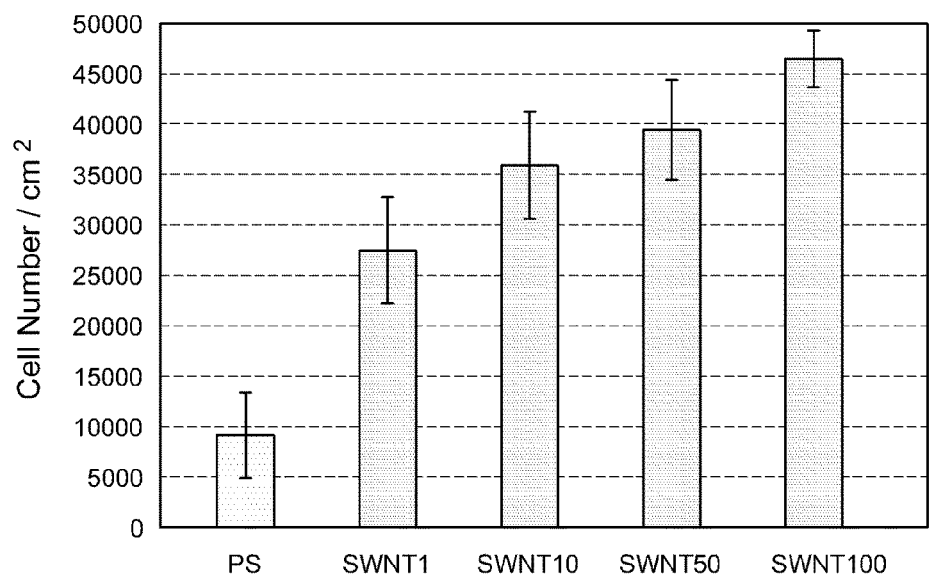
FIG. 2 is a graph showing the results of culture assays according to Example 2.

Using the SWNT1, 50 and 100 dishes produced as described above, the SWNT10 dish produced in Example 1 and an untreated PS dish, SaOs-2 culture assays were carried out in the same way as in Example 1, except for setting the incubation period to two weeks. Those results are shown in Table 2 and FIG. 2. Here, the vertical axis in FIG. 2 represents the cell number per $cm^2$. The ratios of the cell numbers following cultivation in other dishes (relative cell growth ratios) were calculated based on the cell number following cultivation using a PS dish. Those results are also shown in Table 2. When this relative cell growth ratio exceeds 1, a cell growth-promoting effect may be said to exist.

TABLE 2

| Dish | Cell number ($\times 10^3/cm^2$) | Relative cell growth ratio with respect to PS (times) |
|---|---|---|
| SWNT1 | 27.5 | 2.9 |
| SWNT10 | 36.5 | 3.8 |
| SWNT50 | 38.5 | 4.1 |
| SWNT100 | 47.0 | 4.9 |
| PS | 9.5 | 1.0 |

As shown in Table 2 and FIG. 2, in each of the dishes obtained by carrying out treatment wherein a SWNT dispersion was used to form the CNT layer, an increase in cell number greater than that in an untreated PS dish was observed. In dishes obtained by carrying out the SWNT dispersion supply and drying steps at least 20 times (SWNT10, 50 and 100 dishes), especially high cell growth-promoting effects (relative cell growth ratio of at least 3.5 times, and more specifically from 3.8 to 5 times) were observed.

Example 3

A CNT dispersion (also referred to below as "MWNT dispersion") was prepared by adding 1 mg of a CNT material (also referred to below as "MWNT material") obtained by the use of combustion oxidation and hydrochloric acid treatment to purify commercial multilayer CNT (80% purity product manufactured by NanoLab) in 100 mL of anhydrous (99.5%) ethanol, then carrying out ultrasonic dispersion treatment in which 35 kHz ultrasonic vibrations were applied for 30 minutes. Except for using the above MWNT dispersion (MWNT material concentration, 10 mg/L) instead of a SWNT dispersion, a cell culture vessel was produced in the same way as in Example 1. That is, by twice carrying the above MWNT dispersion supply and drying steps in which 50 μL was supplied each time to a 6 cm diameter PS dish (total weight of MWNT material=1 μg), a cell culture vessel with a CNT layer formed on the bottom surface of a PS dish (referred to below as "MWNT1 dish") was produced. A cell culture vessel (MWNT10 dish) was similarly produced by repeating the step of supplying and drying 50 μL of the above MWNT dispersion (total weight of MWNT material=10 μg) 20 times.

An MWNT dispersion was prepared by adding 2 mg of the above MWNT material to 100 mL of anhydrous (99.5%) ethanol and carrying out the ultrasonic dispersion treatment in the same way as described above. A cell culture vessel (MWNT50 dish) was similarly produced by repeating the step of supplying and drying 50 μL of this dispersion (total weight of MWNT material=50 μg) to the above PS dish 50 times.

An MWNT dispersion was prepared by adding 5 mg of the above MWNT material to 100 mL of anhydrous (99.5%) ethanol and carrying out the ultrasonic dispersion treatment in the same way as described above. A cell culture vessel (MWNT100 dish) was similarly produced by repeating the step of supplying and drying 50 μL of this dispersion (total weight of MWNT material=100 μg) to the above PS dish 40 times.

Agglomerates were not observed in any of the MWNT dispersions used above.

Using the MWNT1, 10, 50 and 100 dishes produced above and using also an untreated PS dish, SaOs-2 culture assays (two weeks) were carried out in the same way as in Example 2, and the relative cell growth ratios were similarly calculated. Those results are shown in Table 3.

TABLE 3

| Dish | Cell number ($\times 10^3/cm^2$) | Relative cell growth ratio with respect to PS (times) |
|---|---|---|
| MWNT1 | 12.9 | 1.4 |
| MWNT10 | 22.5 | 2.4 |
| MWNT50 | 24.0 | 2.5 |
| MWNT100 | 18.9 | 2.0 |
| PS | 9.5 | 1.0 |

As shown in Table 3, in each of the dishes obtained by carrying out treatment wherein a MWNT dispersion was used to form the CNT layer, an increase in cell number greater than that in an untreated PS dish was observed. In dishes obtained by carrying out the MWNT dispersion supply and drying steps at least 20 times (MWNT10, 50 and 100 dishes), especially high cell growth-promoting effects (relative cell growth ratio of at least 2 times, and specifically from 2 to 2.5 times) were observed. Based upon a comparison of MWNT and SWNT, dishes treated using SWNT dispersions demonstrated higher effects.

Example 4

Figure 3:
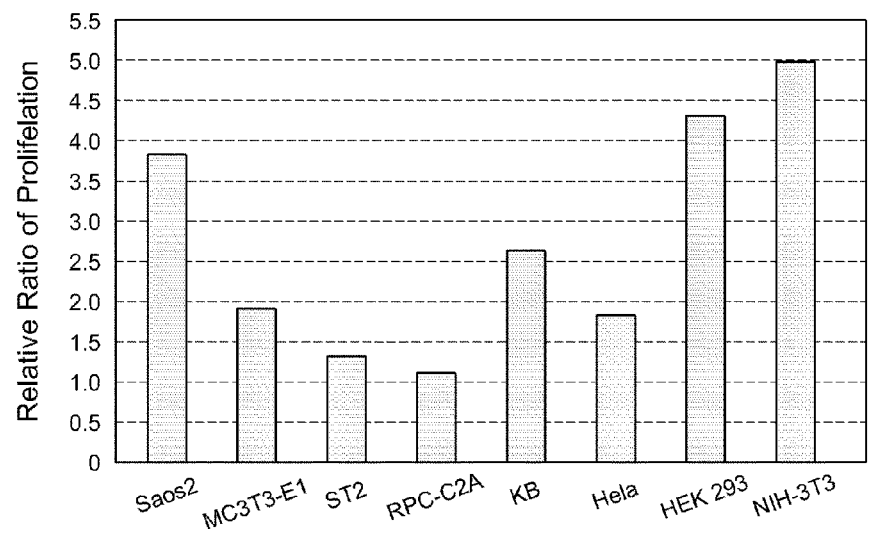
FIG. 3 is a graph showing the results of culture assays according to Example 4.

Using SWNT10 dishes produced as described above and PS dishes, and except for using a culture broth obtained by adding 10 wt % of FBS and 1 wt % of PSN to DMEM media or minimal essential media (MEM), culture assays in which various types of cells are cultivated were carried out under the same culture conditions as in Example 2. The cells used in cultivation were as follows: MC3T3-E1 (mouse skull osteoblast cells), ST2 (mouse bone marrow mesenchymal stem cells), RPC-C2A (rat pulpal cell line), KB (oral squamous cell cancer), Hela (epithelioid cancer of the human cervix), HEK293 (epithelial cells from a human fetus), and NIH-3T3 (fibroblasts from embryonic mouse skin). Each of these types of cells was cultivated until 50% to 70% confluent, and the cell number was counted under an optical microscope. These results are shown in Table 4 and FIG. 3 as the ratio of the cell number following cultivation using a SWNT10 dish relative to the cell number following cultivation using a PS dish (relative cell growth ratio). Here, the vertical axis in FIG. 3 represents the relative cell growth ratio. The relative cell growth ratio for SaOs-2 obtained in Example 2 is shown together with these results in Table 4 and FIG. 3.

TABLE 4

| Cells | Relative cell growth ratio (SWNT10/PS) (times) |
|---|---|
| SaOs-2 | 3.8 |
| MC3T3-E1 | 1.9 |
| ST2 | 1.3 |
| RPC-C2A | 1.2 |
| KB | 2.7 |
| Hela | 1.8 |
| HEK293 | 4.3 |
| NIH-3T3 | 5.0 |

As shown in Table 4 and FIG. 3, as compared to the untreated PS dish, the use of a SWNT10 dish demonstrated cell growth-promoting effects for each of these cell types (the relative cell growth ratios ranged from 1.2 to 5 times).

Example 5

In this example, instead of the culture broth used in Examples 1 to 4 (FBS, 10 wt %), a low-serum culture broth obtained by adding 2 wt % of FBS and 1 wt % of PSN to a DMEM medium was used, and a culture assays were carried out by inoculating this broth with $5 \times 10^4$ cells/dish of SaOs-2. The cell culture vessels used here were as follows: the SWNT10 dish and SWNT100 dish used above, the PS dish and Culture PS dish used above, and also a high cell attachment PS dish (available from Corning under the trade name "CellBind"), a collagen-coated PS dish (produced by IWAKI; labeled in the table and figure as "Collagen"), and a polylysine coated PS dish (produced by IWAKI; labeled in the table and figure as "Poly-Lys") The incubation period was set to two weeks, during which time the culture broth was changed every two days. Except for the above, the cultivation was carried out in the same way as in Example 2, and the cell number following cultivation (spread cell number) was determined. The results obtained are shown in Table 5 and FIG. 4. Here, the vertical axis in FIG. 4 represents the spread cell number per $cm^2$.

TABLE 5

| Dish | Cell number ($\times 10^3/cm^2$) |
|---|---|
| SWNT10 | 10.1 |
| SWNT100 | 18.5 |
| PS | 4.9 |
| Culture PS | 4.5 |
| CellBind | 3.3 |
| Collagen | 2.5 |
| Poly-Lys | 1.0 |

Figure 4:
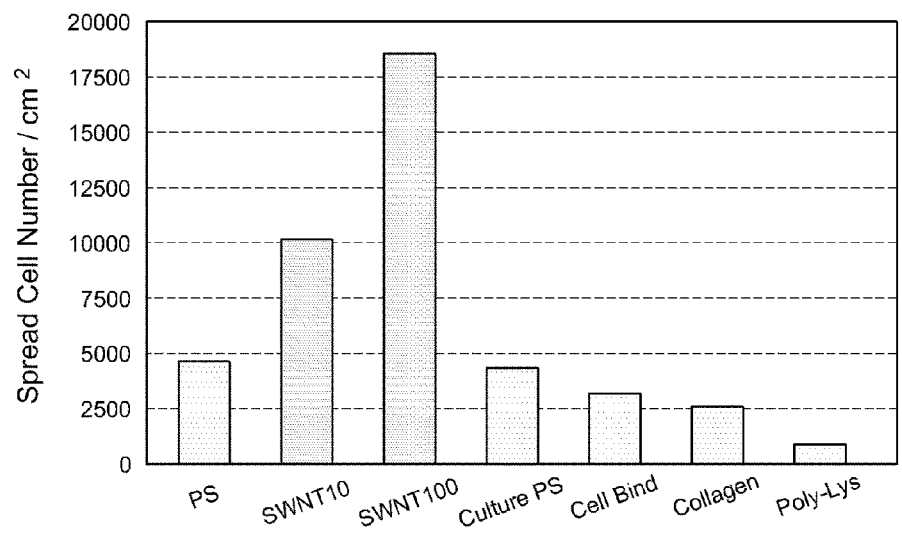
FIG. 4 is a graph showing the results of culture assays according to Example 5.

As shown in Table 5 and FIG. 4, cultivation under these low-serum conditions (FBS, 2 wt %) in each of the commercial cell culture vessels resulted in lower cell numbers than the inoculated number of cells. By contrast, in the dishes obtained by treatment wherein a CNT layer was formed using a SWNT dispersion (the SWNT10 dish and the SWNT100 dish), the cells grew well. Of these two dishes, the SWNT100 dish was confirmed to show an especially high cell growth activity even under such low-serum conditions.

Example 6

Figure 5:
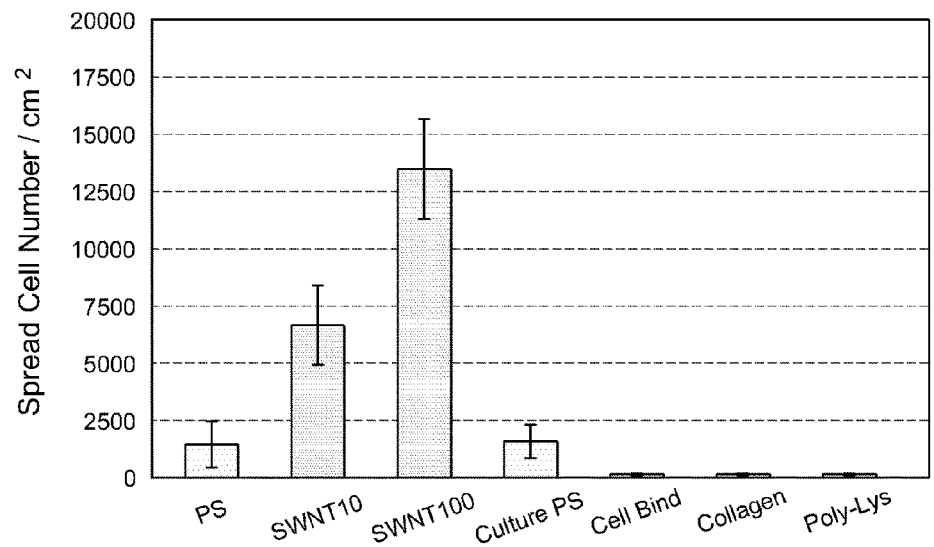
FIG. 5 is a graph showing the results of culture assays according to Example 6.

In this example, a culture broth having an even lower serum concentration than in Example 5 was used; that is, a culture broth obtained by adding 1 wt % of FBS and 1 wt % of PSN to a DMEM medium was used. Except for this, a culture assay in which SaOs-2 was cultured for two weeks was carried out following the same procedure as in Example 5 (during which the culture broth was changed every two days), and the cell number (spread cell number) was determined following cultivation. The results obtained are shown in Table 6 and FIG. 5. Here, the vertical axis in FIG. 5 represents the spread cell number per $cm^2$.

TABLE 6

| Dish | Cell number ($\times 10^3/cm^2$) |
|---|---|
| SWNT10 | 6.7 |
| SWNT100 | 13.5 |
| PS | 1.5 |
| Culture PS | 1.6 |
| CellBind | killed |
| Collagen | killed |
| Poly-Lys | killed |

As shown in Table 6 and FIG. 5, in cultivation under these low-serum conditions (FBS, 1 wt %), in each type of commercial cell culture vessel, either the cell number fell below the inoculation cell number or the cells died. By contrast, in the dishes wherein CNT layer-forming treatment was carried out using a SWNT dispersion (SWNT10 dish and SWNT100 dish), the cells grew well in both cases. Of these, the SWNT100 dish was found to exhibit an especially high cell growth activity even under these low-serum conditions.

Preferred embodiments of the present invention have been described in detail above. However, these embodiments are given merely by way of illustration, and do not limit the scope of the patent claims. The technology recited in the patent claims encompasses various changes and modifications to the embodiments described above.

INDUSTRIAL APPLICABILITY

As explained above, various types of cells can be efficiently cultured (e.g., at a high cell growth ratio as compared to vessels not having a CNT layer) with any of the CNT layers or any of the cell culture vessels having a CNT layer that are disclosed herein. These CNT layers or vessels are able to exhibit excellent cell growth-promoting effects, particularly in cultivation within low-serum media. Generally, cell cultivation in a low-serum medium has various advantages, such as the ability to obtain a more constant growth performance owing to the ability to eliminate or reduce disturbances arising from serum components, the ability to more precisely control the culture conditions, the ability to obtain a cell culture having a higher reliability, and the ease of purification from the culture broth and subsequent processes. Therefore, the inventive CNT layers or cell culture vessels which are able to exhibit excellent growth-promoting effects even in cultivation within a low-serum medium are exceedingly useful.

The invention claimed is:

1. A method of culturing cells comprising:
(a) disposing carbon nanotubes in a dispersion medium to form a mixture thereof, wherein the dispersion medium is a solvent primarily comprised of one of water and a lower alcohol having 1-4 carbons and wherein the carbon nanotubes have a concentration in the mixture of less than or equal to 20 mg/L,
(b) subjecting the mixture to ultrasonic vibrations to form a dispersion, in which the carbon nanotubes are in a highly-dispersed state with no visible agglomerates,
(c) applying an amount of the dispersion in the highly-dispersed state directly to a surface of a vessel such that a resulting carbon nanotube thin-film after drying will contain carbon nanotube material in an amount of at least 0.001 µg and not more than 0.1 µg per $cm^2$,
(d) drying the applied dispersion on the surface to form the carbon nanotube thin-film,
(e) repeating steps (c) and (d) at least 10 times to form a built-up carbon nanotube layer structure having at least 10 layers of carbon nanotube thin-films and such that the built-up carbon nanotube layer structure contains the carbon nanotube material in an amount of at least 0.02 µg and not more than 10 µg per $cm^2$,
(f) sterilizing the vessel having the built-up carbon nanotube layer structure,
(g) disposing cells in the sterilized vessel so that the cells directly contact the built-up carbon nanotube layer structure, and
(h) subjecting the vessel having the cells disposed therein to cell culturing conditions;
wherein steps (c) and (d) are carried out in an environment having a relative humidity of less than or equal to 30% and the dispersion contains substantially no polymer ingredients.

2. A method of culturing cells comprising:
(a) disposing carbon nanotubes in a dispersion medium to form a mixture thereof, wherein the dispersion medium is a solvent primarily comprised of one of water and a lower alcohol having 1-4 carbons and wherein the carbon nanotubes have a concentration in the mixture of less than or equal to 20 mg/L,
(b) subjecting the mixture to ultrasonic vibrations to form a dispersion, in which the carbon nanotubes are in a highly-dispersed state with no visible agglomerates,
(c) applying an amount of the dispersion in the highly-dispersed state directly to a surface of a vessel such that a resulting carbon nanotube thin-film after drying will contain carbon nanotube material in an amount of at least 0.001 µg and not more than 0.1 µg per $cm^2$,
(d) drying the applied dispersion on the surface to form the carbon nanotube thin-film,
(e) repeating steps (c) and (d) at least 10 times to form a built-up carbon nanotube layer structure having at least 10 layers of carbon nanotube thin-films and such that the built-up carbon nanotube layer structure contains the carbon nanotube material in an amount of at least 0.02 µg and not more than 10 µg per $cm^2$,
(f) sterilizing the vessel having the built-up carbon nanotube layer structure,
(g) disposing cells in the sterilized vessel so that the cells directly contact the built-up carbon nanotube layer structure, and
(h) subjecting the vessel having the cells disposed therein to cell culturing conditions;

wherein steps (c) and (d) are carried out at room temperature and atmospheric pressure and the dispersion contains substantially no polymer ingredients.

3. A method of culturing cells comprising:
(a) disposing carbon nanotubes in a dispersion medium to form a mixture thereof, wherein the dispersion medium is a solvent primarily comprised of one of water and a lower alcohol having 1-4 carbons and wherein the carbon nanotubes have a concentration in the mixture of less than or equal to 20 mg/L,
(b) subjecting the mixture to ultrasonic vibrations to form a dispersion, in which the carbon nanotubes are in a highly-dispersed state with no visible agglomerates,
(c) applying an amount of the dispersion in the highly-dispersed state directly to a surface of a vessel such that a resulting carbon nanotube thin-film after drying will contain carbon nanotube material in an amount of at least 0.001 μg and not more than 0.1 μg per cm$^2$,
(d) drying the applied dispersion on the surface to form the carbon nanotube thin-film,
(e) repeating steps (c) and (d) at least 10 times to form a built-up carbon nanotube layer structure having at least 10 layers of carbon nanotube thin-films and such that the built-up carbon nanotube layer structure contains the carbon nanotube material in an amount of at least 0.02 μg and not more than 10 μg per cm$^2$,
(f) sterilizing the vessel having the built-up carbon nanotube layer structure,
(g) disposing cells in the sterilized vessel so that the cells directly contact the built-up carbon nanotube layer structure, and
(h) subjecting the vessel having the cells disposed therein to cell culturing conditions;
wherein steps (c) and (d) are repeated less than or equal to 200 times or between 20-50 times,
wherein the dispersion comprises volatile and non-volatile ingredients and the carbon nanotubes account for at least 95 wt % of the non-volatile ingredients in the dispersion,
wherein steps (c) and (d) are carried out in an environment having a relative humidity of less than or equal to 30% and at room temperature and atmospheric pressure; and the dispersion contains substantially no polymer ingredients.

* * * * *